United States Patent [19]
Kolin

[11] 4,164,939
[45] Aug. 21, 1979

[54] ORTHOGONAL ELECTROMAGNETIC FLOW AND DIAMETER SENSOR SYSTEM

[75] Inventor: Alexander Kolin, Los Angeles, Calif.

[73] Assignee: The Regents of the University of California, Berkeley, Calif.

[21] Appl. No.: 809,539

[22] Filed: Jun. 24, 1977

[51] Int. Cl.$^2$ .............................................. A61B 5/02
[52] U.S. Cl. ................................. 128/692; 73/194 EM
[58] Field of Search .................... 128/2.05 F, 2.05 V, 128/404, 418, 419 P; 73/194 EM

[56] References Cited

U.S. PATENT DOCUMENTS

| | | | |
|---|---|---|---|
| 3,605,726 | 9/1971 | William et al. | 128/2.05 F |
| 3,717,031 | 2/1973 | Biscan | 128/2.05 F X |
| 3,757,773 | 9/1973 | Kolin | 128/2.05 F |
| 3,798,967 | 3/1974 | Gieles et al. | 128/2.05 F X |

OTHER PUBLICATIONS

Berens et al., "New Stable . . . Pacing Loop", Am. J. Cardiology, vol. 34, Sep. 1974, 325–332.
Kolin et al., "An Intra-Arteria . . . Gauge", IEEE Trans on Bio-Med Eng., vol. 18, No. 2, Mar. 1971, pp. 110–114.

*Primary Examiner*—Lee S. Cohen
*Attorney, Agent, or Firm*—Edward H. Loveman

[57] ABSTRACT

An intravascular loop probe includes two lenticular, compressible, resilient, and expansible wire loops disposed in planes substantially mutually perpendicular to each other for operation in a conduit traversed by a magnetic field externally applied. The loops are insulatively joined at the point of maximum curvature. The wires at the open ends of the loops continue as a wire bundle beyond a ground electrode and are cemented together to form a stem for inserting the probe into the conduit via a catheter. Central portions of loop wires are bared to serve as electrodes. The loop terminal wires which form the stem of the probe are connected to external circuitry so that each of the two orthogonal loops is serviced by a separate circuit. The circuitry is such that electromagnetic signals due to flow and magnitude of vascular diameter derived from any type of paired orthogonal flow diameter sensors will be vectorially combined into a signal which does not change as the orthogonal probe is rotated about its axis of symmetry.

13 Claims, 3 Drawing Figures

ORTHOGONAL ELECTROMAGNETIC FLOW AND DIAMETER SENSOR SYSTEM

This invention involves improvements over those described in my prior U.S. Pat. No. 3,757,773, issued Sept. 11, 1973, for "External Field Electromagnetic Flow Sensor-Artery".

In my prior patent I describe a system for the measurement of blood flow and vascular diameter variations, by employing a single intravascular loop probe in an extracorporeal magnetic field. Such measurements may be performed over a wide range of arbitrary probe orientations relative to the magnetic field. The adjustment for optimal probe orientation is desirable for maximum signal, but such adjustments may be quite troublesome. The reason for this difficulty is the failure of the fine wire probe loop to follow continuously the torsion applied to the probe stem which dwells in an intravascular catheter. As a rule the loop orientation will not change for a given angular torsional deformation of the wire stem resulting from a twist applied to the probe stem where it emerges from the catheter. When the angle of twist reaches a certain critical value, the loop will "jump" discontinuously to a new stable orientation from which it can be dislodged only by an additional angular jump produced by additional torsion.

According to the invention the new probe employs two mutually perpendicular loop sensors in a single flow-diameter probe. When one of the loops is unfavorably oriented in the magnetic field, the orientation of the other loop is more favorable. The most unfavorable case is a 45° angle between the magnetic field and the planes of the loops, where the signal drops to 70.7% of the optimal value. By taking the square root of the sum of the squares of the two loop transducer signals, one obtains an output for flow and diameter measurements which is independent of the probe orientation. This operation may be accomplished electronically.

It is therefore a principal object of the present invention to provide a multiple-loop in a catheter for use in measuring rate of flow of conductive fluid in a blood vessel or other conduit, and for measuring the diameter of the blood vessel or conduit, the probe having such a construction that it can yield a measurement signal independent of loop orientation in the conduit for any angle of rotation about the conduit axis with respect to an externally applied magnetic field.

Another object of the present invention is to provide an electromagnetic probe introduceable via an intravascular catheter which has two direction sensitive sensors disposed in mutually perpendicular planes for developing an orientation-independent signal to sense changes in the conduit diameter.

A further object of the present invention is to provide a probe as described with circuitry for rendering constant the fluid flow and/or conduit diameter signals regardless of the orientation of the loops of the probe with respect to an external magnetic field.

These and other objects and many of the attendant advantages of this invention will be readily appreciated as the same becomes better understood by reference to the following detailed description when considered in connection with the accompanying drawings in which.

Figure 1:
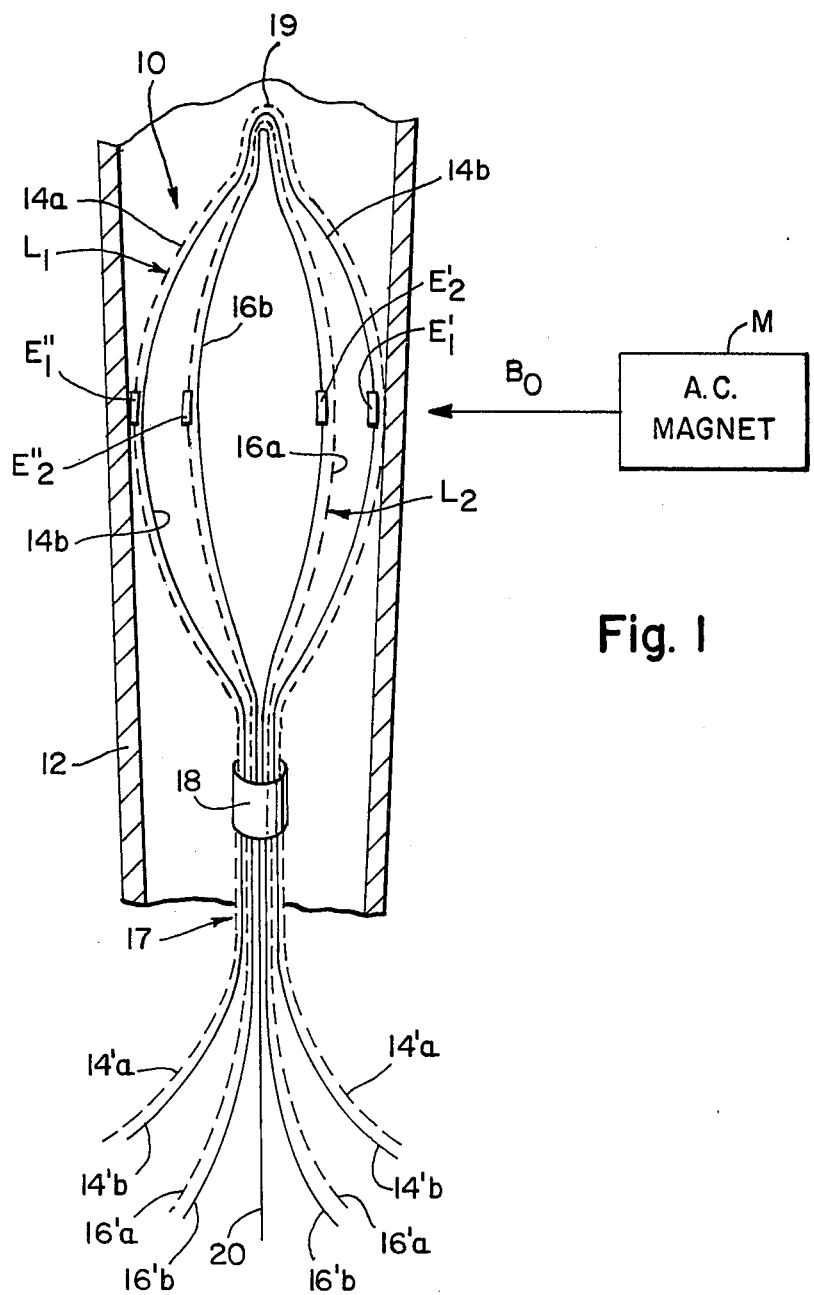
FIG. 1 is a schematic representation of an intravascular loop probe constructed in accordance with the concepts of the present invention, and illustrated as being inserted into a blood vessel.

Referring now to the drawings wherein like reference characters designate like or corresponding parts throughout, there is illustrated in FIG. 1 an orthogonal loop probe generally designated as reference numeral 10 embodying the present invention. This probe forms part of a catheter electromagnetic flow meter. The probe 10 is shown inside a blood vessel 12 whose walls are contacted by electrodes $E'_1$, $E''_1$ of wire loop $L_1$ and by electrodes $E'_2$, $E''_2$ of another wire loop $L_2$. Each of the wire loops $L_1$ and $L_2$ includes two bifilar insulated wires 14a, 14b and 16a, 16b respectively. Before continuing the description of the probe 10, the principle of a single-loop sensor exemplified by loop $L_1$ will be described. The insulation of the wire 14b is removed at a central section along the length of the loop $L_1$ for a few millimeters to constitute one electrode $E'_1$. The insulation of the wire 14a is removed at the same distance along the length of the loop $L_1$ to constitute $E''_1$. These bared wire regions act as flow-sensing electrodes employed in performing the flow meter functions of the loop sensor. At one end of the loop $L_1$ the bifilar wires are secured in a stiff and flexible plastic-enclosed stem 17 below a bare metal ground electrode 18 that is connected to a ground wire 20 which is part of the wire bundle of the stem 17. The loop $L_1$ has a generally lenticular or oval shape and is adapted to be compressed into an elongated configuration so as to pass through a tubing of, for example, 1 to 2.3 millimeters in internal diameter for percutaneous introduction into the blood vessel 12.

The magnetic field is pessimally oriented with respect to the loop $L_1$ for picking up a flow signal since the field is parallel to the line joining the electrodes. The optimal orientation of the magnetic field vector for the loop $L_1$ would be perpendicular to the page. This field orientation would also be optimal for induction of an E.M.F. in the loop $L_1$ (in each of the wires 14a, 14b of the bifilar pair) which acts as a transformer secondary with respect to the A.C. magnet M which plays the role of transformer primary. This induced E.M.F. provides signal information about changes in vascular diameter which is the angiometer function of the loop sensor.

Loop $L_1$ represents the loop sensor in the most unfavorable orientation wherein a zero signal is conveyed to external flow and diameter sensing amplifiers (not shown). Now according to the invention, there is provided a second loop sensor $L_2$ made of insulated bifilar wires 16a, 16b with central bared wire regions constituting electrodes $E'_2$, $E''_2$ of the loop $L_2$. The elongated, compressible loop $L_2$, has an end at the probe terminal 19. There the ends of the loops $L_1$ and $L_2$ can be joined together by insulative means. The other open end of the loop $L_2$ proceeds beyond the ground electrode 18 and is incorporated in the stem 17. Terminal leads 14'a, 14'b, 16'a, 16'b, are connected to the loop wires 14a, 14b, 16a, 16b, respectively which extend within the stem beyond the vessel or conduit 12 for connection to amplifiers and other external circuitry. The structure of the loops $L_1$ and $L_2$ are identical in the double loop sensor configuration. The plane of the loop sensor $L_2$ is perpendicular to that of loop $L_1$. The unfavorable orientation of the loop $L_1$ as mentioned above in FIG. 2 is effectively compensated by the optimal orientation of the loop $L_2$ which is perpendicular to the field. An optimal fluid flow signal is thus picked up by electrodes $E'_2, E''_2$ of loop $L_2$. By connecting terminal leads $16'a, 16'b$ of the loop $L_2$ to an output signal amplifier $A_2$ (FIG. 4) an optimal amplified flow signal is obtained.

Figure 2:
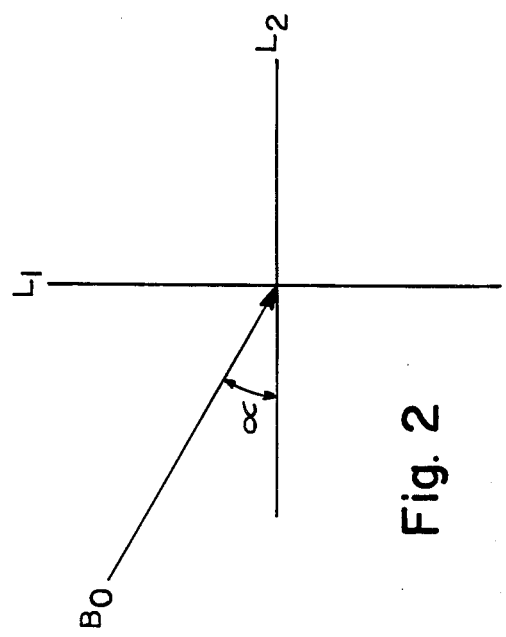
FIG. 2 is a graphic diagram showing orientation of an external magnetic field with respect to probe planes.

In general the double loop sensor probe 10 will form an arbitrary angle $\alpha$ with a vector $B_o$ of the magnetic field; see FIG. 2. It will then be possible to use the output of that loop which yields the larger flow and diameter signals. The signals derived from the loops $L_1$ and $L_2$ become equal to each other for $\alpha = 45°$ as shown in FIG. 2, which depicts the orientation of the magnetic vector $B_o$ relative to the mutually perpendicular planes of the loops $L_1$ and $L_2$. Thus, the most unfavorable orientation of the sensor probe is for $\alpha = 45°$. In this case both of the loops yield a signal which is 70.7% of the optimal value. For any other orientation, one of the two loops will provide a flow and diameter signal closer to 100% of maximum value. The use of probe 10 saves a great deal of time and effort in measuring flow in visceral blood vessels (e.g. superior mesenteric artery and vein) by eliminating need for rotating the subject and for changing the location of the extracorporeal magnet M whose magnetic field is a represented by vector $B_o$ in FIG. 2.

An ideally convenient system would be one in which the flow and diameter signals remain constant regardless of the value of angle $\alpha$. This can be accomplished on the basis of the following considerations. The amplitudes of the loop signal $V_L$ and flow signal $V_F$ are proportional to the component of the magnetic field amplitude $B_o$ which is perpendicular to the plane of the given loop $L_1$ or $L_2$. Using the symbol V for either $V_F$ or $V_L$ depending on whether the flow signal or the diameter measuring loop signal is being considered, we can write for the signals $(V_o)_1$ and $(V_o)_2$ derived from loop $L_1$ or loop $L_2$, $$(V_o)_1 = C\, B_o \cos \alpha \tag{1}$$

$$(V_o)_2 = C\, B_o \sin \alpha \tag{2}$$

The proportionality constant C is, of course, different for the flow signal and loop signal. In general, it depends on the nature of the transducer used.

Adding the squares of equations (1) and (2) we obtain for the summation signal:

$$(V_o)^2 = (V_o)_1^2 + (V_o)_2^2 = C^2 B_o^2 (\sin^2 \alpha + \cos^2 \alpha) = C^2 B_o^2 = \text{constant or } V_o = CB_o = \text{constant.} \tag{3}$$

By summation of the squares of the signals derived from the two loops (or from the two pairs of electrodes) we obtain a resultant signal $V_o$ which is independent from the relative orientation between the loop and the direction of the magnetic field component which lies in the plane which is normal to the blood vessel axis. For best results the vector $B_o$ is oriented so as to maximize the signal $V_o$.

Figure 3:
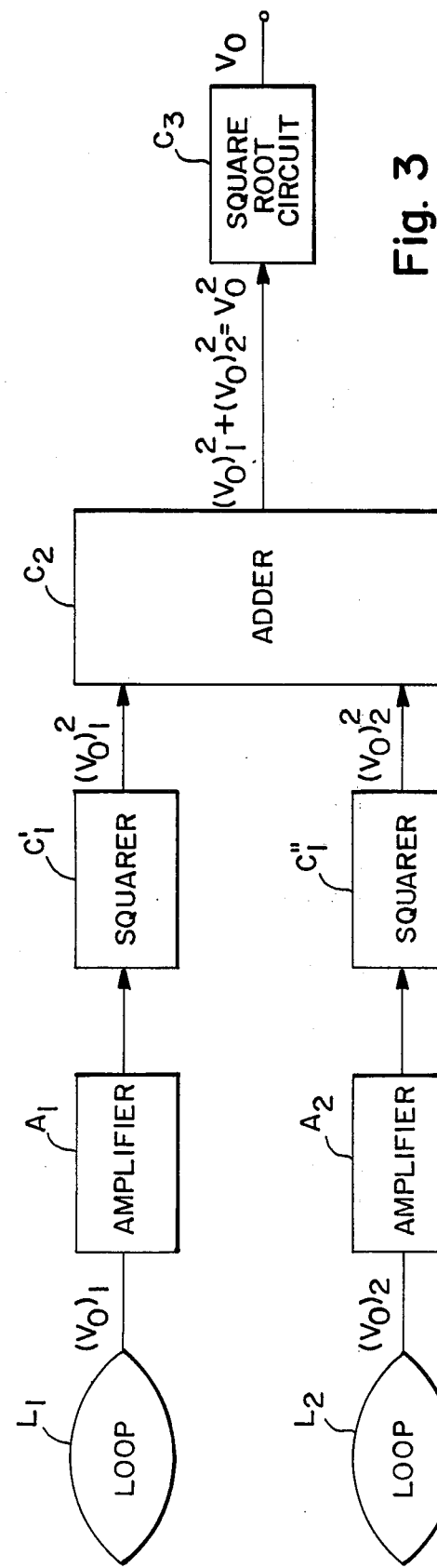
FIG. 3 is a block diagram of the probe loops and associated circuitry for obtaining a maximum flow or diameter signal independent of loop orientation.

FIG. 3 shows a circuit for electronically processing the flow and loop signals derived from the loops $L_1$ and $L_2$ of the probe 10, where a pair of squarer circuits $C'_1$ and $C''_1$ square the incoming loop or flow signals $(V_o)_1$ and $(V_o)_2$ which have been amplified by amplifiers $A_1$, $A_2$. An adder circuit $C_2$ adds the output from the circuits $C'_1$ and $C''_1$. A circuit $C_3$ yields the square root of the signal derived from the adder $C_2$, thus yielding a flow or diameter sensor signal $V_o$ which is independent of the orientation angle of the loops $L_1$, $L_2$ with respect to the magnetic field of the extracorporeal magnet. The squarer circuit, adder circuit and circuit $C_3$ for obtaining the square root are all conventional components and need not be further defined herein.

Although the loop sensors of the probe 10 have been illustrated with one end joined at the point of maximum curvature in some applications it may be desirable to have the loop open i.e. one end of each loop terminates at its respective electrode and the other end of each loop terminates as hereinbefore described at the terminals.

It should be understood that the foregoing relates to only a preferred embodiment of the invention, and that it is intended to cover all changes and modifications of the example of the invention herein chosen for the purposes of the disclosure, which do not constitute departures from the spirit and scope of the invention.

The invention claimed is:

1. An intravascular loop probe comprising:
   a first flat deformable wire loop disposed in a first plane;
   a second flat deformable wire loop disposed in a second plane substantially perpendicular to and centrally intersecting said first plane, said first and second loops defining said probe, each of said loops being closed at one end and having terminals at the other end, said loops being collapsible to an elongated narrow configuration for insertion into a narrow conduit and expansible in a larger conduit; and
   electrode means formed at a diametrically opposite sides of each of said loops for picking up electromagnetically induced signals corresponding to rate of fluid flow in said larger conduit and said loop terminals being connected to said electrode means for yielding an induced signal corresponding to the width of said larger conduit, whereby an externally applied magnetic field will cause induction of voltages in said flowing fluid and said loops in said larger conduit, said voltages corresponding to the rate of fluid flow in said larger conduit, and to the diameter of said larger conduit.

2. An intravascular loop probe as defined in claim 1, wherein said closed end of each of said first and second wire loops are joined together and said loops when expanded in said larger conduit form a generally lenticular loop configuration.

3. An intravascular loop probe as defined in claim 2, further comprising means forming a stem originating at said other ends of said loops to facilitate insertion of said probe through a catheter into said larger conduit and positioning of said probe in said larger conduit.

4. An intravascular loop probe as defined in claim 2, further comprising a ground electrode through which said other ends of said loops are passed and a ground lead connected to said ground electrode for grounding said probe.

5. An intravascular loop probe as defined in claim 3, further comprising insulative means joining said closed ends of said loops to cooperate with said stem in maintaining said loops perpendicular to each other when expanded, and to facilitate insertion of said probe into said larger conduit.

6. An intravascular loop probe as defined in claim 2 further comprising a circuit means connected to said loop terminals for receiving said signals and adapted to maximize the same regardless of the orientation of said loops in said magnetic field.

7. An intravascular loop probe as defined in claim 6, further comprising means of joining said other ends of said loops to form a stiff and flexible stem thereat to facilitate insertion and positioning of said probe in said larger conduit.

8. An intravascular loop probe as defined in claim 7, further comprising a ground electrode through which said other ends of said loops are passed, and a ground lead connected to said electrode for grounding said probe.

9. An intravascular loop probe as defined in claim 7, further comprising terminal leads connected to said terminals of said loops for connection to said circuit means external of said circuit means.

10. An intravascular loop probe as defined in claim 1, further comprising a circuit means connected to said loop terminals for receiving said signals and adapted to maximize the same for a given direction of the axis of said loops regardless of the orientation of said loops in said magnetic field.

11. An intravascular loop probe as defined in claim 10, wherein said circuit means comprises:
 an amplifier means for amplifying said signals;
 a squarer circuit means arranged to square the amplified signals;
 an adder circuit means arranged to add the squared signals; and
 square root circuit means arranged to derive output voltage signals corresponding to the square root of the added squared signals, whereby said output voltage signals will be independent of rotational orientation of said loops within the conduit in said magnetic field.

12. An intravascular loop probe as defined in claim 1, further comprising a circuit means connected to said loop terminals for receiving said signals and adapted to process the same so as to yield a constant signal output, regardless of the orientation of said loops in said magnetic field for a given direction of the axis of said loops.

13. In an intravascular flow sensor for measuring a rate of flow in a first larger diameter biological fluid carrying conduit through which said sensor has been inserted from a second smaller diameter conduit, the improvement comprising:
 two pairs of electrodes, first means for disposing the electrodes of one pair of said pairs of electrodes at opposite ends of a first diameter of said first conduit, second means for disposing the electrodes of the second pair of said pairs of electrodes opposite ends of a second diameter of said first conduit, said second diameter being perpendicular to said first diameter;
 said first and second means including a plurality of resiliently deformable terminable closed wire loops, each closed at one end and having electrical terminals at the other end with one of said electrodes supported thereinbetween said closed loops being deformable to pass through said second smaller diameter conduit and expansible in said larger diameter conduit, whereby an externally applied magnetic field will cause induction of voltages in said flowing fluid in said first conduit which voltages will be picked up by said electrodes, said voltages corresponding to said rate of fluid flowing in said first larger conduit.

* * * * *